United States Patent
Löffler et al.

(10) Patent No.: US 7,323,507 B2
(45) Date of Patent: Jan. 29, 2008

(54) STABLE DISPERSION CONCENTRATE CONSISTING OF A COPOLYMER OF ACRYLOYLDIMETHYLTAURIC ACID AND CYCLIC CARBOXAMIDE AND AN OIL, EMULSIFIER, OR OIL/EMULSIFIER PHASE FOR COSMETIC, PHARMACEUTICAL AND DERMATOLOGICAL COMPOSITIONS, AND METHODS FOR PREPARATION THEREOF

(75) Inventors: Matthias Löffler, Niedernhausen (DE); Roman Morschhäuser, Mainz (DE); Livio Caribé Da Rocha, Sao Paulo (BR)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 204 days.

(21) Appl. No.: 10/388,078

(22) Filed: Mar. 13, 2003

(65) Prior Publication Data

US 2003/0219398 A1 Nov. 27, 2003

(30) Foreign Application Priority Data

Mar. 14, 2002 (DE) .............................. 102 11 140

(51) Int. Cl.
- C08J 3/00 (2006.01)
- C08K 5/05 (2006.01)
- C08K 5/06 (2006.01)
- C08L 37/00 (2006.01)
- C08L 39/00 (2006.01)

(52) U.S. Cl. .......................... 524/379; 424/59; 424/65; 424/78.31; 424/78.35; 424/78.37; 523/105; 523/337; 523/351; 524/267; 524/284; 524/300; 524/306; 524/308; 524/310; 524/313; 524/366; 524/394; 524/548; 524/801; 524/808; 524/817; 524/827; 524/832; 525/283; 525/291; 525/313; 526/258; 526/287

(58) Field of Classification Search ................ 524/801, 524/817, 827, 832, 808, 548, 284, 300, 306, 524/308, 310, 379, 366, 313, 334, 267; 424/59, 424/65, 78.31, 78.35, 78.37; 523/351, 105, 523/337; 525/283, 291, 313; 526/258, 287
See application file for complete search history.

(56) References Cited

U.S. PATENT DOCUMENTS

| | | | |
|---|---|---|---|
| 5,344,655 A * | 9/1994 | Sakai et al. .................. 424/443 |
| 6,120,780 A * | 9/2000 | Dupuis et al. ............... 424/401 |
| 6,355,752 B1 | 3/2002 | Brungs et al. ............... 526/287 |
| 6,437,068 B2 | 8/2002 | Loeffler et al. .............. 526/264 |
| 2001/0029287 A1* | 10/2001 | Loffler et al. ................ 526/263 |
| 2001/0041768 A1* | 11/2001 | Lorant ......................... 524/588 |
| 2002/0176835 A1 | 11/2002 | Loffler et al. ............. 424/70.15 |

FOREIGN PATENT DOCUMENTS

| | | |
|---|---|---|
| EP | 1 028 129 | 4/2000 |
| EP | 1 116 733 | 7/2001 |
| EP | 1 236 464 | 9/2002 |

* cited by examiner

Primary Examiner—Patrick Niland
(74) Attorney, Agent, or Firm—Tod A. Waldrop

(57) ABSTRACT

Dispersion concentrates are claimed which consist of:
I) 10-80% by weight of a crosslinked copolymer obtained by polymerization of 1 to 50% by weight of a cyclic N-vinylcarboxamide and 49.99 to 98.99 by weight of acryloyldimethyltauric acid,
II) 20-90% by weight of a phase selected from the group consisting of an emulsifier, an oil phase, and mixtures thereof, and
III) up to 30% weight water based on the total weight of the stable dispersion concentrate. The stable dispersion concentrate is useful in preparing cosmetic, pharmaceutical, and dermatological compositions.

22 Claims, No Drawings

STABLE DISPERSION CONCENTRATE CONSISTING OF A COPOLYMER OF ACRYLOYLDIMETHYLTAURIC ACID AND CYCLIC CARBOXAMIDE AND AN OIL, EMULSIFIER, OR OIL/EMULSIFIER PHASE FOR COSMETIC, PHARMACEUTICAL AND DERMATOLOGICAL COMPOSITIONS, AND METHODS FOR PREPARATION THEREOF

The present invention relates to dispersion concentrates comprising copolymers based on acryloyldimethyltauric acid or salts thereof (AMPS) and linear and/or cyclic N-vinylcarboxamide.

EP 1 116 733 and EP 1 028 129 describe new classes of polymers based on acryloyldimethyltauric acid or salts thereof. These polymers confer broad performance properties and can be used as thickener, bodying agent, emulsifier, dispersant, lubricant, conditioner and/or stabilizer in cosmetic, dermatological and pharmaceutical compositions.

The copolymers based on AMPS, prepared preferably by precipitation polymerization, in accordance with the prior art are pulverulent substances with performance disadvantages resulting therefrom. In addition to a risk of dust explosion, the dust can harbor dangers in cases of inhalation, and also the storage stability of the powders is impaired by hygroscopicity.

When processing or using the pulverulent products, the dissolution operation (the polymers are preferably incorporated into aqueous media) is in most cases very time-consuming. The dissolution operation of the pulverulent products can, depending on the size of the batch, take one hour and more. In addition, incomplete dissolution/swelling of the pulverulent products is often observed, which leads to a reduction in the quality and stability of the end formulation (formation of lumps). In addition, the processing and/or use of the pulverulent products, requires specific stirring and dispersion devices in order to dissolve, or suspend, the polymers.

The object was to find liquid preparations of the pulverulent polymers based on acryloyldimethyltauric acid or salts thereof, preferably prepared by precipitation polymerization. Preference is given here to dispersions of the polymers in a liquid matrix comprising oil, emulsifier, dispersant and/or water. Preference is given here to liquid-disperse forms with the highest possible polymer proportion, low viscosity coupled with high stability of the dispersion. The oil and emulsifier/dispersant proportions used are preferably cosmetically and pharmaceutically acceptable raw materials.

Surprisingly, it has been found that AMPS copolymers are suitable in an excellent manner for the preparation of dispersion concentrates.

The invention provides dispersion concentrates comprising
I) 10 to 80% by weight, preferably 20 to 60% by weight, particularly preferably 30 to 40% by weight, of a copolymer consisting essentially of
a) 1 to 50% by weight of the repeat structural unit of the formula (1)

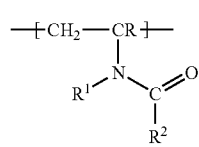

where R, $R^1$ and $R^2$ may be identical or different and are hydrogen or a linear or branched alkyl or alkenyl group having in each case 1 to 30, preferably 1 to 20, in particular 1 to 12, carbon atoms, or $R^1$ and $R^2$ together are a $C_2$-$C_9$-alkylene group,
b) 49.99 to 98.99% by weight of the repeat structural unit of the formula (2)

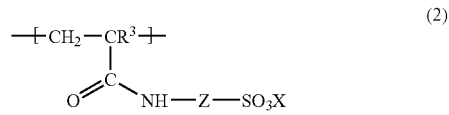

in which $R^3$ is hydrogen, methyl or ethyl, Z is $C_1$-$C_8$-alkylene and X is ammonium, alkali metal or alkaline earth metal ion, and
c) 0.01 to 8% by weight, preferably 0.01 to 5% by weight, of crosslinking structures originating from monomers with at least two olefinic double bonds,
II) 20 to 90% by weight, preferably 30 to 80% by weight, particularly preferably 40 to 60% by weight, of one or more emulsifiers and/or an oil phase, and
III) 0 to 30% by weight, preferably 0 to 10% by weight, particularly preferably 0 to 5% by weight, of water.

Preferably, the dispersion concentrates according to the invention comprise copolymers consisting of 2 to 30% by weight, in particular 3 to 15% by weight, of structural units of the formula (1), preferably derived from N-vinylpyrrolidone, 69.5 to 97.5% by weight, in particular 84.5 to 96.5% by weight, of structural units of the formula (2), preferably derived from the ammonium salt of 2-acrylamido-2-methylpropanesulfonic acid, and 0.2 to 3% by weight, in particular 0.5 to 2% by weight, of crosslinking structures originating from monomers with at least two olefinic double bonds. The copolymers can also comprise mixtures of different structural units within the formula (1), preferably mixtures of monomers with cyclic and open carboxamide groups.

The mixing ratio can vary here within any desired limits.

Crosslinking structures which originate from monomers with at least two olefinic double bonds are preferably derived from acrylic or methacrylic allyl esters, dipropylene glycol diallyl ether, polyglycol diallyl ether, triethylene glycol divinyl ether, hydroquinone diallyl ether, tetraallyloxyethane or other allyl or vinyl ethers of multifunctional alcohols, tetraethylene glycol diacrylate, triallylamine, trimethylolpropane diallyl ether, methylenebisacrylamide or divinylbenzene.

Particularly preferably, the crosslinking structures are derived from monomers of the formula (3),

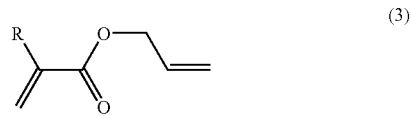

in which R is hydrogen, methyl or ethyl.

The copolymers which form the basis of the dispersion concentrates according to the invention are prepared as described in EP 1 116 733 and EP 1 028 129, by dissolving or dispersing the monomers corresponding to the repeat structural units of the formulae (1) and (2) in a protic solvent, adding one or more crosslinkers with at least two olefinic double bonds to this solution or dispersion, and starting the polymerization in a manner known per se by adding a free radical-forming compound.

The acryloyldimethyltaurates may be the inorganic or organic salts of acryloyldimethyltauric acid (acrylamidopropyl-2-methyl-2-sulfonic acid). Preference is given to the $Li^+$, $Na^+$, $K^+$, $Mg^{++}$, $Ca^{++}$, $Al^{+++}$ and/or $NH_4^+$ salts.

The degree of neutralization of the acryloyldimethyltauric acid can be between 0 and 100%, particular preference being given to a degree of neutralization of more than 80%.

As well as comprising the copolymer, the dispersion concentrates according to the invention also comprise one or more emulsifiers and/or an oil phase in the stated amount. If emulsifiers are used as the sole component II, the proportion of the oil phase is thus 0% and, accordingly, the proportion of the emulsifiers is 0%, if the component II consists only of an oil phase. Preference is given to using a mixture of emulsifier and oil phase as second component.

Suitable emulsifiers are addition products of from 0 to 30 mol of alkylene oxide, in particular ethylene oxide, propylene oxide, butylene oxide onto linear fatty alcohols having 8 to 22 carbon atoms, onto fatty acids having 12 to 22 carbon atoms, onto alkylphenols having 8 to 15 carbon atoms in the alkyl group and onto sorbitan esters; ($C_{12}$-$C_{18}$)-fatty acid mono- and diesters of addition products of from 0 to 30 mol of ethylene oxide onto glycerol; glycerol mono- and diesters and sorbitan mono- and diesters of saturated and unsaturated fatty acids having 6 to 22 carbon atoms and optionally their ethylene oxide addition products; addition products of from 15 to 60 mol of ethylene oxide onto castor oil and/or hydrogenated castor oil; polyol and, in particular, polyglycerol esters, such as, for example, polyglycerol polyricinoleate and polyglycerol poly-12-hydroxystearate. Preference is given to liquid fatty acid esters which may either be ethoxylated (PEG-10 polyglyceryl-2-laurate) or as nonethoxylated (polyglyceryl-2 sesquiisostearate).

Preferred emulsifiers are sorbitol esters prepared by reacting sorbitol with fatty acid methyl esters or fatty acid triglycerides. The fatty acid radical in the fatty acid methyl esters and fatty acid triglycerides generally comprises 8 to 22 carbon atoms and can be straight-chain or branched, saturated or unsaturated. Examples thereof are palmitic acid, stearic acid, lauric acid, linoleic acid, linolenic acid, isostearic acid or oleic acid. Suitable fatty acid triglycerides are all natural animal or vegetable oils, fats and waxes, for example olive oil, rapeseed oil, palm kernel oil, sunflower oil, coconut oil, linseed oil, castor oil, soybean oil, optionally also in refined or hydrogenated form. Since these natural fats, oils and waxes are normally mixtures of fatty acids of varying chain length, this also applies to the fatty acid radicals in the sorbitol esters used according to the invention. The sorbitol esters used according to the invention can also be alkoxylated, preferably ethoxylated.

In addition, it is possible to use anionic emulsifiers, such as ethoxylated and nonethoxylated mono-, di- or triphosphoric esters, but also cationic emulsifiers, such as mono-, di- and trialkyl quats and their polymeric derivatives.

Likewise suitable are mixtures of compounds from two or more of these classes of substance.

The dispersions according to the invention can comprise, instead of the emulsifier or in a mixture with an emulsifier, one or more oil(s), preferably from the group of hydrocarbons, ester oils, vegetable oils and silicone oils. Hydrocarbon oils are, for example, those linear or branched, saturated or unsaturated $C_7$-$C_{40}$-carbon chains, for example Vaseline, dodecane, isododecane, cholesterol, lanolin, hydrogenated polyisobutylenes, docosanes, hexadecane, isohexadecane, paraffins and isoparaffins;

oils of vegetable origin, in particular liquid triglycerides, such as sunflower oil, corn oil, soybean oil, rice oil, jojoba oil, babusscu oil, pumpkin oil, grapeseed oil, sesame oil, walnut oil, apricot oil, macadamia oil, avocado oil, sweet almond oil, lady's smock oil, castor oil, olive oil, groundnut oil, rapeseed oil and coconut oil;

oils of animal origin, for example beef tallow, perhydrosqualene, lanolin.

Also suitable are synthetic oils, such as purcellin oil, linear and/or branched fatty alcohols and fatty esters, preferably Guerbet alcohols having 6 to 18, preferably 8 to 10, carbon atoms; esters of linear ($C_6$-$C_{13}$)-fatty acids with linear ($C_6$-$C_{20}$)-fatty alcohols; esters of branched ($C_6$-$C_{13}$)-carboxylic acids with linear ($C_6$-$C_{20}$)-fatty alcohols, esters of linear ($C_6$-$C_{18}$)-fatty acids with branched alcohols, in particular 2-ethylhexanol; esters of linear and/or branched fatty acids with polyhydric alcohols (such as, for example, dimerdiol or trimerdiol) and/or Guerbet alcohols; alcohol esters of $C_1$-$C_{10}$-carboxylic acids or $C_2$-$C_{30}$-dicarboxylic acids, $C_1$-$C_{30}$-carboxylic monoesters and polyesters of sugar, $C_1$-$C_{30}$-monoesters and polyesters of glycerol;

waxes, such as beeswax, paraffin wax or microcrystalline waxes, optionally in combination with hydrophilic waxes, such as, for example, cetylstearyl alcohol; fluorinated and perfluorinated oils;

Monoglycerides of $C_1$-$C_{30}$-carboxylic acids, diglycerides of $C_1$-$C_{30}$-carboxylic acids, triglycerides of $C_1$-$C_{30}$-carboxylic acids, for example triglycerides of caprylic/capric acids, ethylene glycol monoesters of $C_1$-$C_{30}$-carboxylic acids, ethylene glycol diesters of $C_1$-$C_{30}$-carboxylic acids, propylene glycol monoesters of $C_1$-$C_{30}$-carboxylic acids, propylene glycol diesters of $C_1$-$C_{30}$-carboxylic acids, and propoxylated and ethoxylated derivatives of the abovementioned classes of compound.

The dispersions according to the invention can additionally also comprise 0 to 30% by weight, preferably 0 to 10% by weight, particularly preferably 0 to 5% by weight, of water.

The dispersion concentrates according to the invention can be prepared in various ways, an inverse emulsion polymerization or an inverse mini-emulsion polymerization being as preferred as a physical mixing of copolymer with oil and emulsifier and optionally water. The physical mixing is preferably carried out by mixing oil phase and emulsifier(s) at 10 to 60° C., preferably at room temperature, then adding copolymer(s) to about 40% by weight of the oil/emulsifier phase over a period of from 10 to 60 min, preferably about 30 min, with vigorous stirring. During this, a homogeneous paste forms. If necessary, a small amount of water can be added to improve processing. Then, the remaining oil/emulsifier phase is added with stirring and the mixture is stirred to homogeneity for a number of hours. A liquid, pourable dispersion is formed.

The dispersion concentrates according to the invention are suitable as thickener, bodying agent, emulsifier, solubilizer, dispersant, lubricant, adhesive, conditioner and/or stabilizer—in an excellent manner for the formulation of cosmetic, pharmaceutical and dermatological compositions, in particular of oil-in-water emulsions in the form of creams, lotions, cleansing milk, cream gels, spray emulsions, e.g. body lotions, aftersun lotions, sunscreen compositions and deodorant sprays.

The advantage of these dispersion concentrates is that the copolymers defined above are present here in an administration form which permits simple preparation of pharmaceutical and cosmetic preparations based on these copolymers. The dispersion concentrates according to the invention are surprisingly pourable and storage-stable despite their high proportion of copolymer.

The dispersion concentrates according to the invention are used in the cosmetic and pharmaceutical preparations in amounts by weight such that polymer concentrations of from 0.01 to 10% by weight, preferably 0.1 to 5% by weight, particularly preferably 0.5 to 3% by weight, based on the finished compositions, result.

Such preparations can comprise anionic, cationic, nonionic, zwitterionic and/or amphoteric surfactants, and also further auxiliaries and additives, cationic polymers, film formers, super fatty agents, stabilizers, biogenic active ingredients, glycerol, preservatives, pearlizing agents, dyes and fragrances, solvents, opacifiers, and also protein derivatives, such as gelatin, collagen hydrolysates, natural and synthetic-based polypeptides, egg yolk, lecithin, lanolin and lanolin derivatives, fatty alcohols, silicones, deodorizing agents, substances with keratolytic and keratoplastic action, enzymes and carrier substances. Furthermore, antimicrobially effective agents can be added to the compositions according to the invention.

In addition, such preparations can comprise organic solvents. In principle, suitable organic solvents are all mono- or polyhydric alcohols. Preference is given to using alcohols having 1 to 4 carbon atoms, such as ethanol, propanol, isopropanol, n-butanol, isobutanol, t-butanol, glycerol and mixtures of said alcohols. Further preferred alcohols are polyethylene glycols with a relative molecular mass below 2000. In particular, the use of polyethylene glycol with a relative molecular mass between 200 and 600 and in amounts up to 45% by weight and of polyethylene glycol with a relative molecular mass between 400 and 600 in amounts of from 5 to 25% by weight is preferred. Further suitable solvents are, for example, triacetin (glycerol triacetate) and 1-methoxy-2-propanol. Short-chain anionic surfactants, in particular arylsulfonates, for example cumene- or toluenesulfonate, have a hydrotropic effect.

The examples below of dispersion concentrates with AMPS polymers serve to illustrate the subject matter of the invention in more detail without limiting it thereto (the percentages are percentages by weight).

Various dispersion concentrates with differing emulsifier and oil concentration were prepared. For this, ®Aristoflex AVC and ®Aristoflex AVC-1 (Clariant) were used.

Table 1 shows examples of dispersion concentrates which are flowable and storage-stable (sedimentation upon storage at 25° C. for 3 weeks).

|   |                        | A  | B  | C    | D  | E  | F  | G    | H  |
|---|------------------------|----|----|------|----|----|----|------|----|
| 1 | Aristoflex AVC         | 36 | 36 | 36   | 30 |    |    |      |    |
| 2 | Aristoflex AVC-1       |    |    |      |    | 36 | 36 | 36   | 30 |
| 3 | Hostacerin DGI         |    | 30 | 3    | 51 |    | 30 | 3    | 51 |
| 4 | Hostaphat KL 340 D     | 18 | 18 | 2    | 13 | 18 | 18 | 2    | 13 |
| 5 | Emulsogen SRO          | 30 |    |      |    | 30 |    |      |    |
| 6 | Mineral oil, low-viscosity | 8 |   | 29.5 | 6  | 8  |    | 29.5 | 6  |
| 7 | Isopropyl palmitate    | 8  |    | 29.5 |    | 8  |    | 29.5 |    |
| 8 | Myritol 318            |    | 16 |      |    |    | 16 |      |    |

These dispersion concentrates were prepared as follows:
1. Mix oil and emulsifier component 3-8 and initially introduce one third of the mixture.
2. Within half an hour, add polymer 1-2 with stirring at 400 rpm.
3. After-stir for half an hour then add the remaining mixture of the oil and emulsifier component.
4. After-stir for a further 5 hours.

Structure of the commercial products used:

|   |                    | INCI name                                              |
|---|--------------------|--------------------------------------------------------|
| 1 | Aristoflex AVC     | Ammonium Acryloyldimethyltaurate/VP Copolymer          |
| 2 | Aristoflex AVC-1   | Ammonium Arcryloyldimethyltaurate/Vinylformamide Copolymer |
| 3 | Hostacerin DGI     | Polyglyceryl-2-Sesquiisostearate                       |
| 4 | Hostaphat KL 340 D | Trilaureth-4 Phosphate                                 |
| 5 | Emulsogen SRO      | Rapeseed Oil Sorbitol Esters                           |
| 6 |                    | Mineral oil, low-viscosity                             |
| 7 |                    | Isopropyl Palmitate                                    |
| 8 | Myritol 318        | Caprylic/Capric Triglyceride                           |

Examples for using the dispersion concentrates according to the invention in the preparation of cosmetic preparations.

EXAMPLE 1

Moisturizing Lotion

| A |                         | 7.00%  |
|---|-------------------------|--------|
|   | Almond oil              | 7.00%  |
|   | Cyclomethicones         | 5.00%  |
| B | Dispersion concentrate C| 4.00%  |
| C | Glycerol                | 7.00%  |
|   | Water                   | ad 100%|
|   | Preservative            | q.s.   |
| D | Fragrance               | 0.30%  |

Preparation

I Mix A and B.

II Stir solution C into I.

III Add D to II.

IV Homogenize

V pH 5.5

EXAMPLE 2

Sunscreen Lotion

| A |                         | 5.00%   |
|---|-------------------------|---------|
|   | Vaseline                | 5.00%   |
|   | Paraffin oil            | 10.00%  |
|   | Dispersion concentrate A| 2.00%   |
|   | Tocopheryl acetate      | 1.00%   |
|   | Octyl methoxycinnamate  | 2.00%   |
|   | Parsol 1789             | 0.20%   |
| B | Ethanol                 | 10.00%  |
| C | Butylene glycol         | 5.00%   |
|   | Water                   | ad 100% |

Preparation

I A and C are heated separately to 75° C., then combined and cooled, with stirring, to 65° C., homogenized and cooled further to 35° C., II Stir B into 1, homogenize and cool to room temperature

EXAMPLE 3

O/W Skin Milk

| | Composition | |
|---|---|---|
| A | Isopropyl palmitate | 4.00% |
| | Almond oil 5.00% | 4.00% |
| | Wheatgerm oil | 1.00% |
| | ® Cetiol SN (Henkel) | 8.00% |
| | Cetearyl isononanoate | |
| B | Dispersion concentrate G | 1.50% |
| C | Water | ad 100% |
| D | Fragrances | 0.30% |

Preparation
I Add B to A with stirring
II Stir C and D into I
III Homogenize emulsion

The invention claimed is:
1. A liquid dispersion concentrate consisting essentially of:
I) 20% to 80% by weight of the liquid dispersion concentrate, of a copolymer consisting essentially of
a) 1% to 50% by weight of the copolymer, of the repeat structural unit of the formula (1)

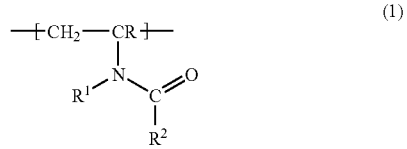

where R, $R^1$ and $R^2$ may be identical or different and are hydrogen or a linear or branched alkyl or alkenyl group having in each case 1 to 30 carbon atoms, and $R^1$ and $R^2$ together are a $C_2$-$C_9$-alkylene group,
b) 49.99% to 98.99% by weight of the copolymer, of the repeat structural unit of the formula (2)

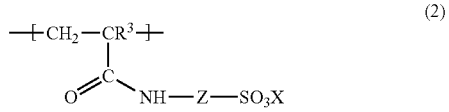

in which $R^3$ is hydrogen, methyl or ethyl, Z is ($C_1$-$C_8$)-alkylene, and X is an ammonium, alkali metal or alkaline earth metal ion
and
c) 0.01% to 8% by weight of the copolymer, of crosslinking structures which originate from monomers having at least two olefinic double bonds,
II) 20% to 80% by weight of the liquid dispersion concentrate, of a phase selected from the group consisting of: one or more emulsifier, wherein the emulsifier is selected from the group consisting of:
addition products of from 0 to 30 mol of alkylene oxide onto fatty acids having 12 to 22 carbon atoms, addition products of from 0 to 30 mol of alkylene oxide onto alkylphenols having 8 to 15 carbon atoms in the alkyl group, and/or
addition products of from 0 to 30 mol of alkylene oxide onto sorbitan esters;
($C_{12}$-$C_{18}$)-fatty acid mono- and diesters of addition products of from 0 to 30 mol of ethylene oxide onto glycerol;
glycerol mono- and diesters and sorbitan mono- and diesters of saturated and unsaturated fatty acids having 6 to 22 carbon atoms and optionally their ethylene oxide addition products;
addition products of from 15 to 60 mol of ethylene oxide onto castor oil and/or hydrogenated castor oil;
polyol esters;
liquid fatty acid esters which may either be ethoxylated or nonethoxylated;
sorbitol esters prepared by reacting sorbitol with fatty acid methyl esters or fatty acid triglycerides, wherein the fatty acid radical in the fatty acid methyl esters and fatty acid triglycerides comprises 8 to 22 carbon atoms and can be straight-chain or branched, saturated or unsaturated, wherein the sorbitol esters can also be alkoxylated;
anionic or cationic emulsifiers;
and mixtures of compounds from two or more of these classes of substance;
an oil phase, wherein the oil phase is selected from the group consisting of:
hydrocarbons, ester oils, vegetable oils, and silicone oils, and a mixture thereof, and
III) 0% to 5% by weight of the liquid dispersion concentrate, of water, wherein the liquid dispersion is pourable.

2. The liquid dispersion concentrate of claim 1, wherein the copolymer consists of 2% to 30% by weight of the copolymer, of the structural units of the formula (1), 69.5% to 97.5% by weight of the copolymer, of the structural unit of the formula (2), and 0.2% to 3% by weight of the copolymer, of crosslinking structures originating from monomers with at least two olefinic double bonds.

3. The liquid dispersion concentrate of claim 1, wherein the crosslinking structures are derived from the group consisting of acrylic or methacrylic allyl esters, dipropylene glycol diallyl ether, polyglycol diallyl ether, triethylene glycol divinyl ether, hydroquinone diallyl ether, tetraallyloxyethane, allyl or vinyl ethers of multifunctional alcohols, tetraethylene glycol diacrylate, triallylamine, trimethylolpropane diallyl ether, methylenebiacrylamide, divinylbenzene, and mixtures thereof.

4. The liquid dispersion concentrate of claim 1, wherein the copolymer has the crosslinking structures derived from monomers of formula (3)

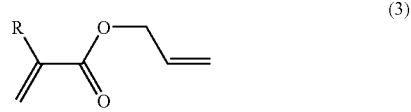

in which R is hydrogen, methyl or ethyl.

5. The liquid dispersion concentrate of claim 1, which comprises 20% to 60% by weight of the liquid dispersion concentrate, of the copolymer.

6. The liquid dispersion concentrate of claim 1, which comprises 30% to 40% by weight of the liquid dispersion concentrate, of the copolymer.

7. The liquid dispersion concentrate of claim 1, which comprises 30% to 80% by weight of the liquid dispersion concentrate, of component II.

8. The liquid dispersion concentrate of claim 1, which comprises 40% to 60% by weight of the liquid dispersion concentrate, of component II.

9. A method for improving the manufacture of a preparation selected from the group consisting of cosmetic, pharmaceutical and dermatological preparations, said method comprising adding to the preparation the liquid dispersion concentrate of claim 1.

10. The liquid dispersion concentrate of claim 1, wherein R is hydrogen or a linear or branched alkyl or alkenyl group having 1 to 20 carbon atoms.

11. The liquid dispersion concentrate of claim 1, wherein R is hydrogen or a linear or branched alkyl or alkenyl group having 1 to 12 carbon atoms.

12. The liquid dispersion concentrate of claim 1, wherein the crosslinking structures which originate from monomers having at least two olefinic double bonds range from 0.01% to 5% weight of the copolymer.

13. The liquid dispersion concentrate of claim 3 wherein the copolymer consists of 3% to 15% by weight of the structural units of formula (1).

14. The liquid dispersion concentrate of claim 3 wherein the copolymer of the structural units of formula (1) is derived from N-vinylpyrrolidone.

15. The liquid dispersion concentrate of claim 3 wherein the copolymer consists of 84.5% to 96.5% by weight of the structural units of formula (2).

16. The liquid dispersion concentrate of claim 3 wherein the copolymer consists of 0.5% to 2% by weight of the crosslinking structures.

17. The liquid dispersion concentrate according to claim 1 wherein $R^1$ and $R^2$ together are a $C_2$-$C_9$-alkylene group.

18. A liquid dispersion concentrate consisting of:
I) 20% to 80% by weight of the liquid dispersion concentrate, of a copolymer consisting essentially of
   a) 1 to 50% by weight of the copolymer, of the repeat structural unit of the formula (1)

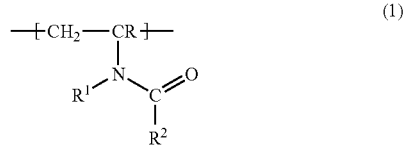

(1)

where R, $R^1$ and $R^2$ may be identical or different and are hydrogen or a linear or branched alkyl or alkenyl group having in each case 1 to 30 carbon atoms, and $R^1$ and $R^2$ together are a $C_2$-$C_9$-alkylene group,
   b) 49.99% to 98.99% by weight of the copolymer, of the repeat structural unit of the formula (2)

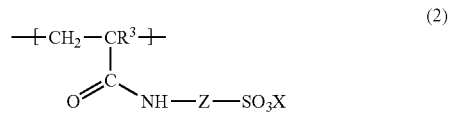

(2)

in which $R^3$ is hydrogen, methyl or ethyl, Z is $(C_1$-$C_8)$-alkylene, and X is an ammonium, alkali metal or alkaline earth metal ion
and
   c) 0.01% to 8% by weight of the copolymer, of crosslinking structures which originate from monomers having at least two olefinic double bonds,
II) 20% to 80% by weight of the liquid dispersion concentrate, of a phase selected from the group consisting of one or more emulsifier, an oil phase selected from the group consisting of: hydrocarbons, ester oils, vegetable oils, and silicone oils, and a mixture thereof, and
III) 0% to 5% by weight of the liquid dispersion concentrate, of water, wherein the liquid dispersion is pourable.

19. The liquid dispersion concentrate according to claim 18 wherein the weight of copolymer is 20% to 40% of the weight of the liquid dispersion concentrate.

20. The liquid dispersion concentrate of claim 1, wherein R is hydrogen or a linear or branched alkyl or alkenyl group having in each case 1 to 30 carbon atoms, and $R^1$ and $R^2$ together are a $C_2$-$C_9$-alkylene group.

21. The liquid dispersion concentrate according to claim 1 wherein the one or more emulsifier is selected from the group consisting of: liquid fatty acid esters which may either be ethoxylated or nonethoxylated; sorbitol esters prepared by reacting sorbitol with fatty acid methyl esters or fatty acid triglycerides wherein the fatty acid radicals in the fatty acid methyl esters and fatty acid triglycerides comprise 8 to 22 carbon atoms and can be straight-chain or branched, saturated or unsaturated and wherein the sorbitol esters used according to the invention can also be alkoxylated; ethoxylated or nonethoxylated mono-, di- or triphosphoric esters, and mixtures thereof.

22. The liquid dispersion concentrate according to claim 1, wherein the one or more emulsifier is a polyglycerol ester.

* * * * *